(12) United States Patent
Haechler et al.

(10) Patent No.: US 8,361,160 B2
(45) Date of Patent: Jan. 29, 2013

(54) PATELLA TRACKING

(75) Inventors: Joerg Haechler, Baar (CH); John Naybour, Beeston (GB)

(73) Assignee: DePuy Orthopadie GmbH (DE)

( * ) Notice: Subject to any disclaimer, the term of this patent is extended or adjusted under 35 U.S.C. 154(b) by 907 days.

(21) Appl. No.: 12/296,406

(22) PCT Filed: Apr. 5, 2007

(86) PCT No.: PCT/GB2007/001321
§ 371 (c)(1),
(2), (4) Date: Mar. 20, 2009

(87) PCT Pub. No.: WO2007/128991
PCT Pub. Date: Nov. 15, 2007

(65) Prior Publication Data
US 2009/0264737 A1    Oct. 22, 2009

(30) Foreign Application Priority Data
Apr. 7, 2006 (GB) .................................. 0607027.0

(51) Int. Cl.
*A61F 2/38* (2006.01)
*A61F 2/00* (2006.01)
*A61B 17/58* (2006.01)
*A61B 17/60* (2006.01)

(52) U.S. Cl. ............... 623/20.2; 623/20.18; 606/102

(58) Field of Classification Search .............. 623/20.2, 623/20.18; 606/102
See application file for complete search history.

(56) References Cited

U.S. PATENT DOCUMENTS

| | | | | |
|---|---|---|---|---|
| 4,285,070 A | * | 8/1981 | Averill | ............... 623/20.2 |
| 5,702,465 A | | 12/1997 | Burkinshaw | |
| 5,723,016 A | | 3/1998 | Minns | |
| 6,589,248 B1 | * | 7/2003 | Hughes | ............... 606/102 |
| 2003/0212403 A1 | | 11/2003 | Swanson | |
| 2005/0101966 A1 | | 5/2005 | Lavallee | |
| 2005/0251065 A1 | | 11/2005 | Henning | |
| 2006/0052792 A1 | * | 3/2006 | Boettiger et al. | ............... 606/88 |

FOREIGN PATENT DOCUMENTS

| | | |
|---|---|---|
| EP | 1582184 A | 10/2005 |
| EP | 1582184 A1 | 10/2005 |
| FR | 2726758 A1 | 5/1996 |
| FR | 2737848 A1 | 2/1997 |
| GB | 2277034 A | 10/1994 |

(Continued)

OTHER PUBLICATIONS

PCT Written Opinion, 7 pages.

(Continued)

*Primary Examiner* — Kevin T Truong
*Assistant Examiner* — David Bates (57) ABSTRACT

A device and methods for use in determining the trajectory of a patella of a patient during a navigated knee replacement surgical procedure are described. The device includes a first component including a mounting for attachment to a posterior surface of the patient's patella and a second component having an outer surface presenting a formation adapted to engage with a femoral part of the patient's knee. A slider mechanism allows the second component to translate relative to the first component in a substantially medial-lateral direction of the patient when the first component is attached to the patient's patella. The device can be used in a method to help determine the medial-lateral position for a patella implant.

3 Claims, 4 Drawing Sheets

FOREIGN PATENT DOCUMENTS

WO  WO 2004/049941 A1  6/2004
WO  WO 2004/075767 A   9/2004

OTHER PUBLICATIONS

International Search Report, dated Sep. 11, 2007, 9 pages.

UK Search Report, dated Jul. 28, 2006, 1 page.
Japanese Application 2009-503663 Office Action with references cited dated Apr. 17, 2012.

* cited by examiner

PATELLA TRACKING

The present invention relates to tracking the patella, and in particular to apparatus, instruments and methods for allowing the patella to be tracked in order to improve surgical procedures carried out on the knee.

Currently, little consideration is given to the patella in knee arthroplasty procedures. In particular, little consideration is given to how prosthetic implant components of the knee joint may affect the patella. Further, there is little consideration given to how the patient's patella may interact with an implanted knee joint component. Also, little consideration is given to trying to recreate the original behaviour or motion of the patient's patella.

WO 2004/075767 describes a patella referencing device which can be attached to the patella to allow the position of the patella to be determined in scan assisted surgical operations. A main body attaches to the patella and a reference array is removably connectable to the main body in at least two different positions. However, this referencing device does not allow the kinematic behaviour of the patella to be determined.

It would therefore be advantageous to be able to determine the kinematic behaviour of the patient's patella so as to improve the results of knee replacement surgery.

The present invention provides a trial component which can be used to determine the trajectory of the tracked patella as part of a knee replacement surgical procedure so as to help guide the surgical procedure, e.g. the placement of implanted components, so that the kinematic behaviour of the patella can be appropriately reproduced in the replacement knee joint.

According to a first aspect of the present invention, there is provided a device for use in determining the trajectory of a patella of a patient during a navigated knee replacement surgical procedure. The device can include a first component for attaching to the patient's patella and a second component attached to the first component and which can be linearly translated relative to the first component. The first component can include a mounting by which the first component can be attached to a posterior surface of the patient's patella. The second component can have an outer surface which presents a formation adapted to engage with a femoral part of the patient's knee in use. A slider mechanism can also be provided by which the second component can translate relative to the first component in a substantially medial-lateral direction of the patient when the first component is attached to the patient's patella in use.

By allowing the part which can interact with the femur to slide relative to the part which can be attached to the patella, the medial-lateral position of the patella can be adjusted to allow the kinematic behaviour of the patella to be more flexibly and comprehensively determined. By using the device of the present invention, an optimum position for an actual patella implant can be determined thereby improving the resulting prosthetic knee joint.

Herein, "a femoral part of the patient's knee" is intended to include the patient's anatomical femur as well as an implanted femoral component of the patient's knee, whether it be a trial implant, the actual prosthetic implant or any other implant.

The device can further comprise a lock mechanism. The lock mechanism can be operated to prevent translation of the second component relative to the first component. Hence, the device can be arranged to have the first and second components at various fixed relative displacements thereby allowing the affect of the femoral part on the patella to be determined for different potential patella implant positions.

The lock mechanism can be accessible via the outer surface of the second component so as to make it easier to set and release the lock with the device in situ in use.

The lock mechanism can interact between the first component and the second component. Alternatively, or additionally, the lock component can interact with the slider mechanism to prevent relative translation of the first and second components.

The device can further comprise a resilient biasing means which can act to resist translation of the second component relative to the first component. The resilient biasing means makes the device behave more closely to the behaviour of a real patella. More than one resilient biasing means can be provided, for example two, which can be arranged to act in opposition to each other. The or each resilient biasing means can be of any suitable type, such as a rubber body or a spring, such as a metal coil spring. The or each resilient biasing means can interact with the sliding mechanism. Preferably, the or each resilient biasing means is located within the sliding mechanism and engage between a stationary part and a movable part of the sliding mechanism.

The first component can be substantially planar. The sliding mechanism can be configured so that the second component translates in a plane substantially parallel to the plane of the first component. Hence, the second component will translate in a plane substantially parallel to the plane of the surface of the patella to which the device is attached in use and so there is no need to adjust the orientation of the device relative to the patella.

The device can further comprise at least one marker trackable by a tracking system. The maker can be attached to the second component. This allows the medial-lateral displacement of the second component to be easily determined. The maker can be attached within the second component. A maker can be attached to the first component. This allows the position of the first component to be determined. The maker can be attached within the first component. Preferably a marker is attached to the first component and a further marker is attached to the second component. Preferably the or each marker does not require line of sight communication with the tracking system. The or each marker can be a wired or wireless marker. Preferably, the or each marker includes at lease one magnetic field sensor.

According to a further aspect of the invention, there is provided a kit including a device according to the first aspect of the invention and at least one of: a marker trackable by a tracking system for attaching to a patella; a plurality of resilient biasing means for use with the device; a further device according to the first aspect of the invention having a different size.

According to a further aspect of the invention, there is provided a method for assessing the positioning of a patella implant for a patient during a navigated knee replacement surgical procedure, the method comprising: attaching a patella implant to the posterior of the patient's patella by a first component, wherein a second component can translate relative to the first component in the medial-lateral direction; determining the trajectory of the patella as the knee joint is articulated while the second component is free to translate relative to the first component; and determining the medial-lateral displacement of the second component relative to the patella over at least a part of the trajectory.

Hence, a preferred medial-lateral off set position of the patella implant can be determined.

The trajectory of the patella as the knee joint is articulated can be determined while the second component is free to translate relative to the first component and while the second component is fixed in the medial-lateral direction relative to the first component. The method can further comprise comparing the trajectories.

According to a further aspect of the invention, there is provided a computer implemented method for assessing the position of a patella implant for a patient during a navigated knee replacement surgical procedure, wherein a trial patella implant is attached to the posterior of the patient's patella by a first component of the trial patella implant and a second component of the trial patella implant can translate relative to the first component in the medial-lateral direction, the method comprising: determining the trajectory of the patella as the knee joint is articulated while the second component is free to translate relative to the first component from tracking data for the patella; and determining the medial-lateral displacement of the second component relative to the patella over at least a part of the trajectory from tracking data.

The method can further comprise determining the trajectory of the patella as the knee joint is articulated while the second component is fixed in the medial-lateral direction relative to the first component from tracking data for the patella. The method can also include displaying a comparison of the trajectories.

In the method aspects of the invention, the trajectory can be relative to a femoral and/or tibial component or part of the knee joint. The component or part can be an anatomical part of the patient's knee or an artificial part, such as a trial or implant, of the patient's knee.

A further aspect of the invention provides computer program code including instructions which when executed by a data processor carry out any of the computer implemented method aspects of the invention. A computer readable medium bearing such computer program code provides a further aspect of the invention.

An embodiment of the invention will now be described, by way of example only, and with reference to the accompanying drawings, in which.

Similar items in different Figures share common reference numerals unless indicated otherwise.

Figure 1:
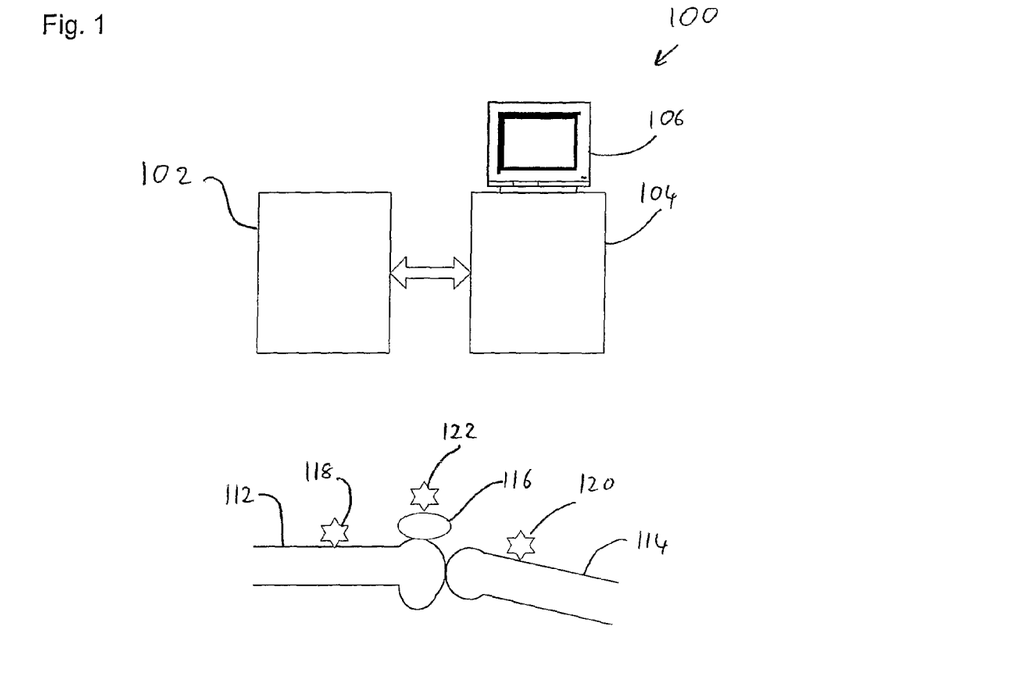
FIG. 1 shows a schematic block diagram of a computer assisted surgery system with which the device of the present invention can be used.

With reference to FIG. 1 there is shown a schematic block diagram of a computer assisted surgery (CAS) system 100 with which the device of the present invention can be used in a navigated knee arthroplasty procedure. The CAS system includes a tracking subsystem 102 in communication with a main computer based system 104 which includes a display device 106. Display device provides graphical representations of the relative positions of various entities, such as body parts, implants, instruments and tools, which are part of the surgical procedure, and graphical representations of positional data, such as important anatomical positions or axes or the planned positions of implants, instruments or tools. The display allows image guided surgery to be carried out as is well known generally in the art.

FIG. 1 also shows a schematic representation 110 of the knee joint of a patient, including the femur 112, the tibia 114 and the patella 116. Each of the femur, tibia and patella has a respective marker 118, 120, 122 attached, each of which is independently trackable by the tracking subsystem 102 which provides tracking data to the computer system 104 to allow the position and orientation of the marked entity to be determined in the reference frame of the tracking system. Instruments, implants and other entities to be navigated during the surgical procedure have trackable markers also.

Various types of tracking technology can be used, including wire based and wireless tracking technologies, such as ultrasonic, infrared, and electromagnetic. A commonly used infrared tracking technology uses a pair of cameras to capture images of reference arrays each having a plurality of reflective spheres thereon. An example electromagnetic tracking technology uses a marker including three mutually perpendicular sensor coils to determine the magnetic field strength of a time varying magnetic field and is described in greater detail in international patent publication no WO 2005/084572, and other documents referenced therein, which are incorporated herein by reference for all purposes.

Computer system 104 includes software implementing a number of functions, including software defining a workflow for carrying out the surgical procedure which generally includes software for registration of the patient, implants and instruments with the reference frame of the tracking system, and software for planning the surgical procedure.

Figure 2:
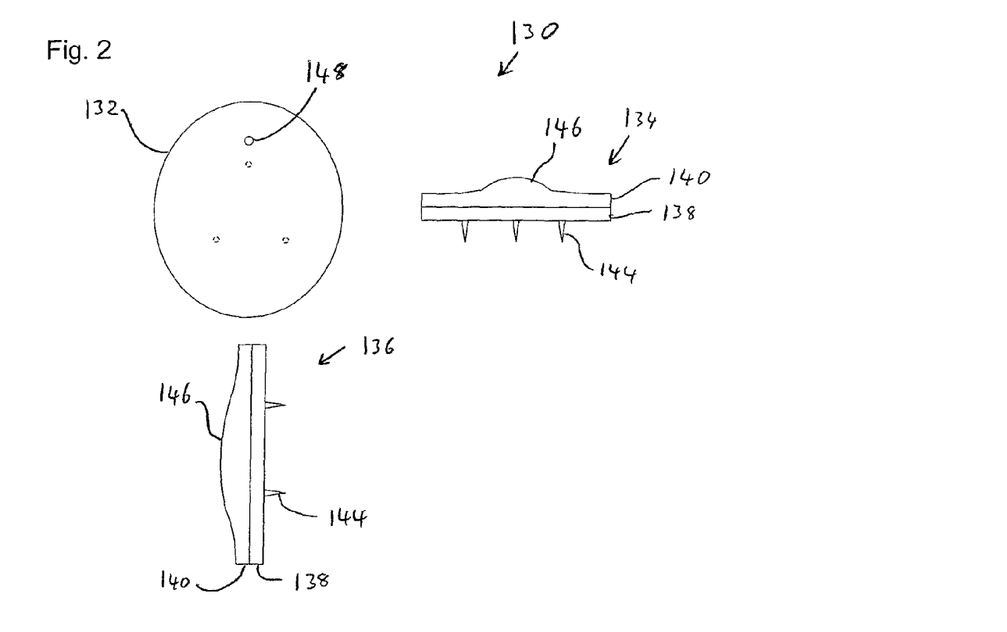
FIG. 2 shows respective schematic plan, side and end views of a first embodiment of a trackable patella implant according to the present invention.

With reference to FIG. 2 there is shown a device 130 for use during a navigated knee arthroplasty procedure to determine the trajectory of the patella during flexion and extension of the knee so as to assist in carrying out the procedure. As used herein "trajectory" generally refers to the path followed by an entity in space. In particular, the trajectory of the patella can be determined absolutely, in which the path of the patella in the reference frame of the tracking system is determined by tracking. Also, the trajectory of the patella can be determined relatively, such as relative to a femoral component of the knee joint, for example, the actual anatomical knee of the patient, or an implant or trial part of a knee joint femoral prosthesis, by tracking. The trajectory of the patella can also be determined relative to a tibial component of the knee joint, for example, the actual anatomical tibial knee part of the patient, or an implant or trial part of a knee joint tibial prosthesis, by tracking. This can be useful in allowing the rotation of the tibia relative to the patella track to be determined.

FIG. 2 shows a plan view 132, end view 134 in a superior-inferior direction and side view 136 in a medial lateral-direction of the device 130. The device can be used as a trial implant, or in other embodiments can be the actual prosthetic implant which is permanently implanted in the patient.

The trial implant includes a first portion 138 and second portion 140 each having a generally circular or ovoid shape. The trial implant can be provided in a range of different sizes, for example having diameters, or major axes, from approximately 24 mm to 36 mm. The first component is generally planar and can be made of a biocompatible metal, such as stainless steel or titanium. Three sharp metal spikes 144 (shown in ghost lines in plan view 132) project from a rearward face of the first component and provide a mounting by which the trial can be attached to a resected posterior face of the patella in use. The second component is attached to the first component by a slider mechanism as will be described with reference to FIG. 4 below, so that the second component can translate linearly relative to the first component and in a plane generally parallel to the plane of the first component.

The second component has a generally smooth dome shaped formation on an outward surface which is shaped to generally correspond to the typical posterior surface of a patella which engages with the sulcus groove of the femur. In use the formation may engage with the corresponding groove portion of the patient's original femur or with the corresponding groove portion of a femoral implant, depending on the stage of the surgical procedure as will be explained in greater detail below. A threaded bore 148 extends through the second component to the interface between the first and second components and receives a grub screw 149 or similar threaded component which provides a lock mechanism to fix the relative position of the first and second components. The second component can be made of a biocompatible plastics material, such as acetyl or polyethylene.

Figure 3:
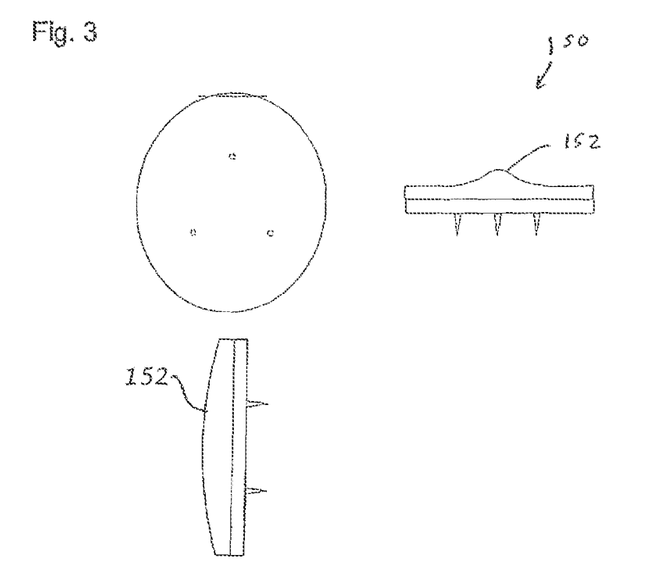
FIG. 3 shows respective schematic plan, side and end views of a second embodiment of a trackable patella implant according to the present invention.

FIG. 3 shows a second embodiment 150 of the patella trial implant similar to that shown in FIG. 2, but in which the formation 152 of the second component is shaped more like a smooth ridge extending along the superior-inferior axis of the device.

Figure 4:
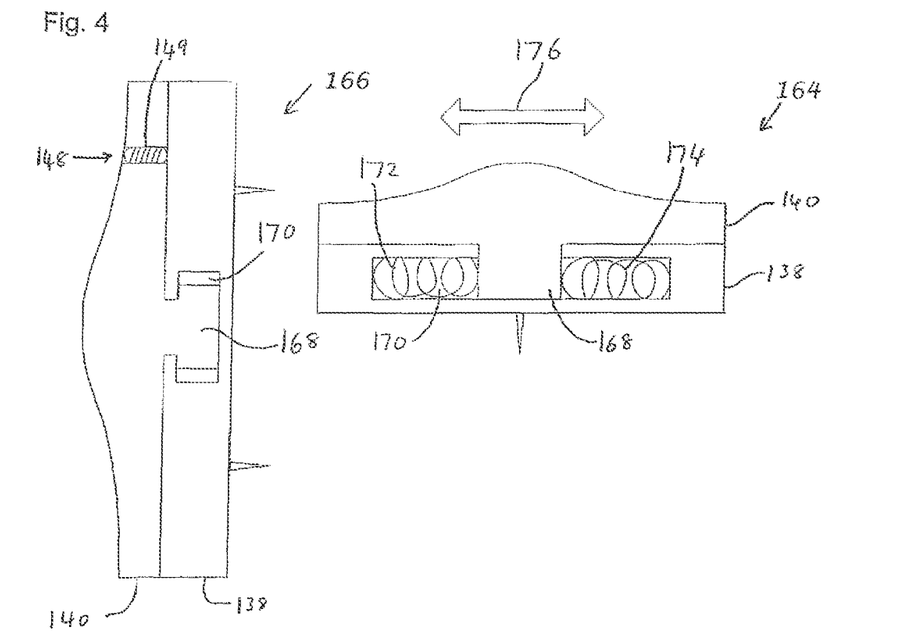
FIG. 4 shows respective cross sectional views of the implant shown in FIG. 2 in the medial-lateral and superior-inferior directions.

FIG. 4 shows a cross sectional view 164 through the centre of the trial implant 130 along the medial-lateral axis and a cross sectional view 166 through the centre of the trial implant 130 along the superior-inferior axis. A slider mechanism joins the first 138 and second components 140. The slider mechanism is provided by a generally T shaped projection 168 from the inner surface of the second component which runs in and along a recessed channel 170 extending along the medial-lateral axis of the device. First 172 and second 174 springs are located in the channel on respective sides of the projection and provide a resilient biasing means to control the translation of the second component relative to the first. FIG. 4 also better illustrates the locking mechanism. The friction caused by screwing grub screw 149 against the inner surface of the first component allows the relative positions of the second and first components in the medial-lateral direction to be fixed while unscrewing grub screw 149 allows the second component to slide freely in the medial-lateral direction as illustrated by double headed arrow 176.

It is not essential that the device be provided with resilient biasing means, but it is preferred in order for the trial implant to more accurately mimic the behaviour of a real patella. Different strength springs can be used in different applications of the trial device. For example, stronger springs can be used for larger people and different strength springs can be used for male and female patients or patients of different ages, e.g. adults and children.

In other embodiments, each or both of the first and second components 138, 140 can include a marker or sensor, for example a magnetic filed sensor, by which the first and/or second components can be tracked so that the positions of the first and/or second components can be determined by the tracking system. Hence, the relative displacement of the second component 140 and the first component can be determined by tracking them and determining their trajectories. If a trackable marker or sensor is provided only in the second component, then it is still possible to determine the displacement of that component relative to the patella as the patella itself can also be tracked. Providing a trackable marker in the first component allows the position of the first component to be determined, for example if it is useful to be able to determine the position of the first component relative to the position of the patella can be separately tracked.

In one embodiment of the device, the marker or markers are be provided as integral parts of the first and/or second components of the device, for example by being included within the first and/or second components. Alternatively, the marker or markers can be attached to the first and/or second components.

Figure 5A:
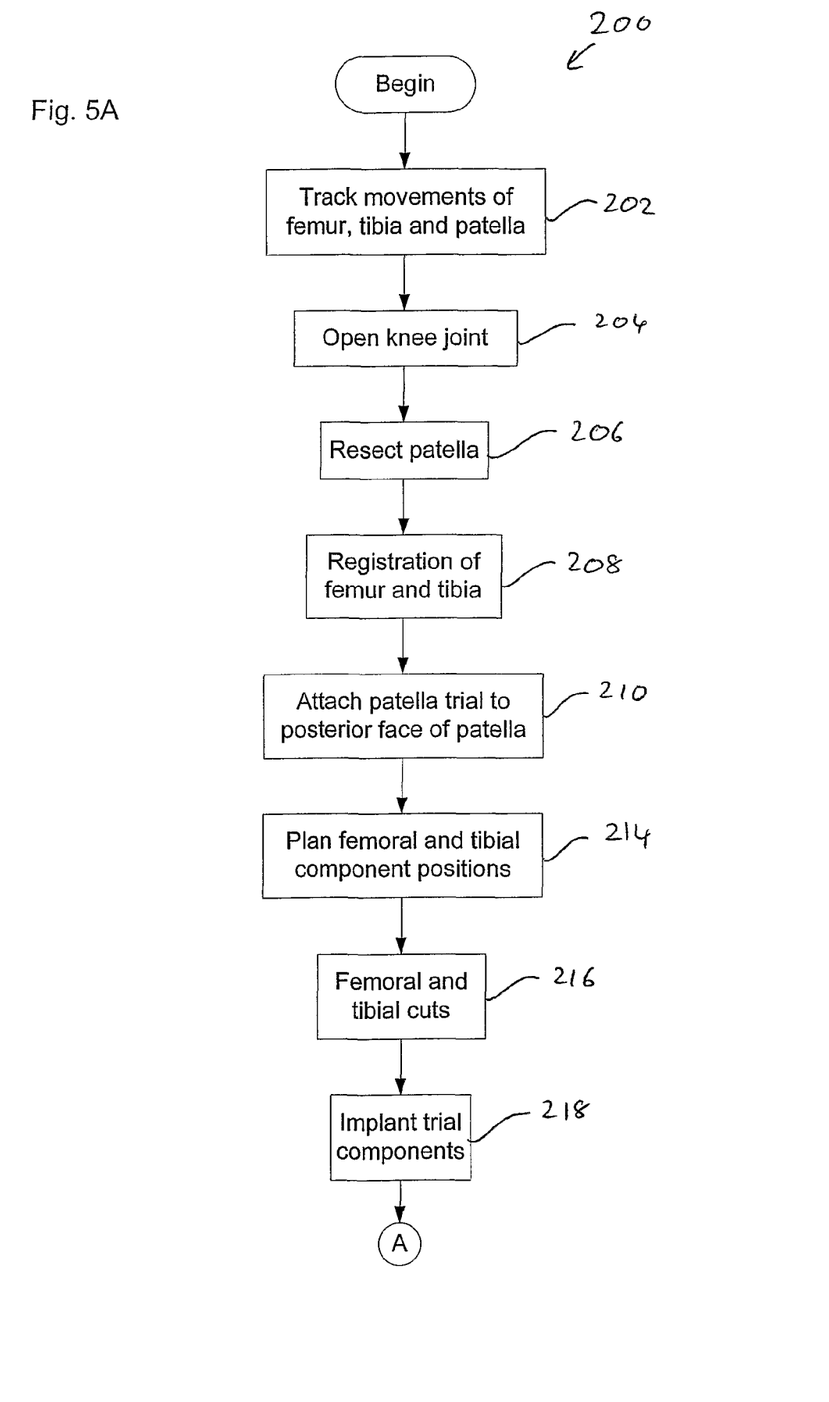
FIGS. 5A and 5B show a flow chart illustrating a method according to the invention of using the implant.
Figure 5B:
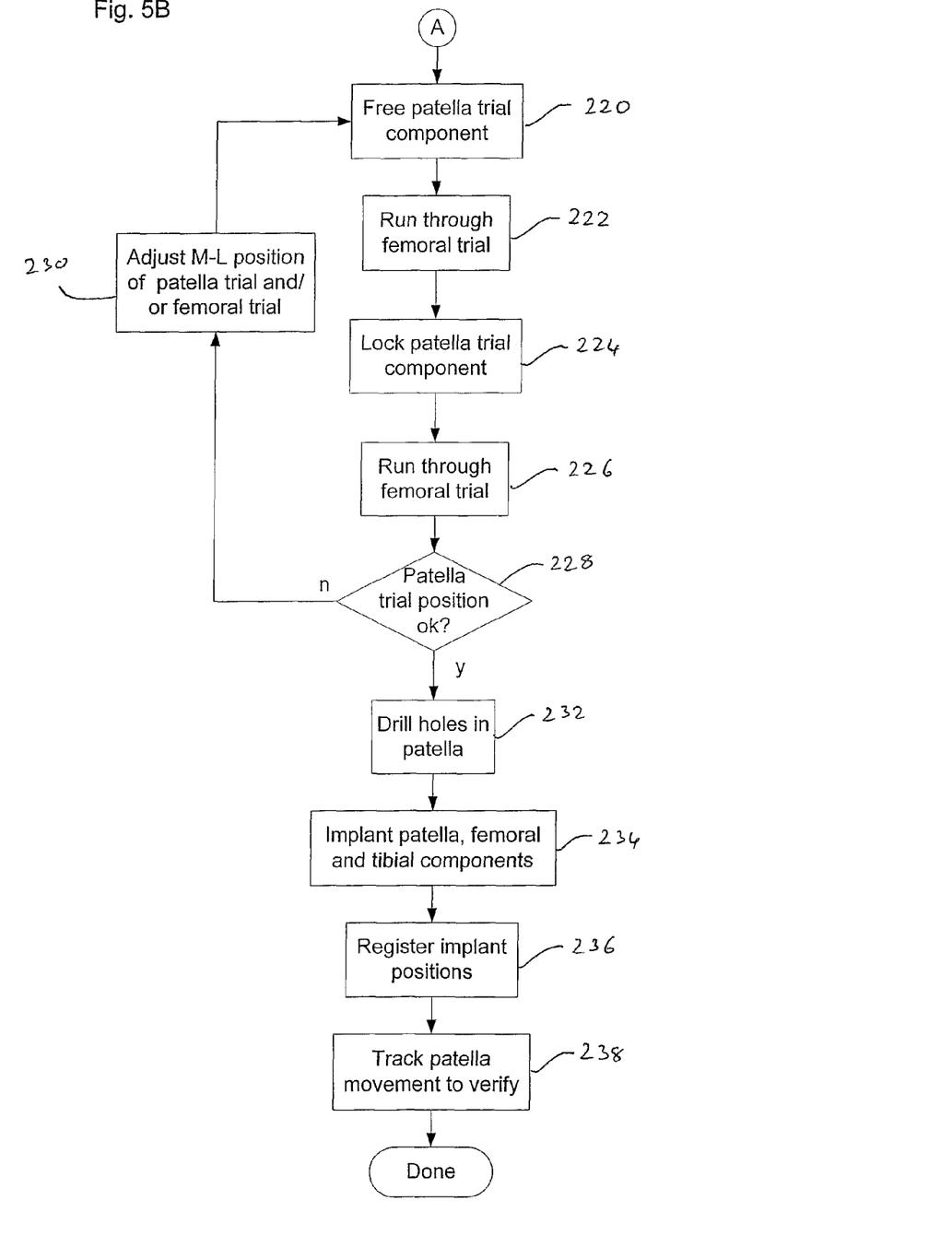

FIGS. 5A and 5B show a flow chart illustrating a computer aided surgical procedure 200 according to the invention and in which the trial implant device can be used. Many of the steps have counterpart operations carried out by processes of the CAS system and those computer processes are also an aspect of the invention.

The method begins and trackable markers 118, 120, 122 are attached to the femur, tibia and patella. It is also possible to provide a marker attached to the first component of the device rather than directly attached to the patella itself. In this way the marker is indirectly attached to the patella by the first component. Irrespective of whether the marker is attached directly to the patella, or indirectly via the first component, all that is required is that there is a fixed positional relationship between the marker for tracking the patella position and the patella. However, it is preferred if the marker 122 is attached to the patella in case it is necessary to re-locate the device on the patella.

At step 202, the position of the femur, tibia and patella are tracked as the knee joint is articulated and the CAS system captures tracking data which represents the trajectory of the patella as the knee joint is flexed, for example between flexion and extension. As indicated above, tracking data is captured that allows the position in space of the patella itself to be determined as the knee joint is flexed and also to allow the position in space of the patella relative to the femoral part of the knee joint to be determined ("the patella relative trajectory"). That is, tracking data is captured which allows the path that the patella runs through over the femoral component of the knee as the knee joint is articulated to be determined in absolute and relative terms. The initial patella relative trajectory provides a reference trajectory corresponding to the preferred trajectory of the patella for the original knee joint. This allows the 'natural' trajectory of the patella, that is, the trajectory that the patella would like to follow for the knee joint in its current pre-operative state, to be determined.

Then at step 204, the knee joint is opened and at step 206 the posterior surface of the patella is resected to leave a substantially flat surface to which the trial implant is to be attached. Then at step 208, the tibia and femur are registered with the CAS system and the mechanical axes of the tibia and femur and the mechanical axis of the leg are determined using any suitable technique. For example, the mechanical axes can be determined by using a trackable pointer to capture various anatomical features having a known relationship with the mechanical axes and/or the motion of the tibia and/or femur can be tracked to determine the mechanical axes, e.g. by pivoting the femur about the femoral head. The tibia and femur can be registered using a statistical shape model technique in which a cloud of points over the surface of the tibia and femur are captured and then generic models of a tibia and femur are morphed to provide a customised model of the tibia and femur. In other embodiments, registration techniques using pre- or intra-operatively captured images of the patient can be used.

After registration, the trial implant is attached to the resected posterior face of the patella with the longitudinal axis of the slider mechanism generally parallel to the medial-lateral direction of the patient's knee joint and so that the formation on the outward side of the second component will engage the sulcus groove in the femur when the patella is in its normal position. The trial implant is pushed against the resected surface of the patella and the three spikes act to securely fasten the trial implant to the patella so that the first component does not move relative to the patella. The trial is attached with the first and second components locked so that the second component cannot slide relative to the first component.

Then, the positions of the femoral and tibial implant components are planned. This can include determining the size of components to use, their relative positions, their relative orientations and their positions and orientations relative to the bones. For example, the medial-lateral position of the implants, their internal/external rotations and the bone cut positions may be planned. The mechanical axes of the tibia, femur and leg may be used to constrain the planned implant positions and also the trajectory of the patella may be used to constrain the planned position of the femoral component by requiring the sulcus groove, or equivalent thereof, of the femoral component to be positioned and angled to result in an at least similar trajectory for the patella.

After planning of the femoral and tibial components, at step 216 the femoral and tibial cuts are made and at step 218 trial femoral and tibial implants are inserted. Then the medial-lateral position of the patella implant trial can be adjusted in an iterative way to fine tune the position of the patella implant and/or femoral implant so as to try and reproduce the original patella trajectory and/or alter the patella trajectory to improve the kinematic knee joint performance. A number of steps 220 to 230 may be repeated in various combinations and omitting various of the steps in a generally iterative patella implant trial adjustment process and the flow chart of FIG. 5B is by way of general explanation and illustration of these steps rather than requiring fixed adherence to the particular sequence and number of steps illustrated and described herein.

Initially the patella trial is unlocked so that the second component is free to slide relative to first component. Then at step 222, the position of the patella is tracked relative to the femoral component and also the positions of the first and second components are tracked as the knee joint is articulated through a flexion to extension cycle. The tracking data captured can then be used to determine the trajectory that the patella itself would like to follow independently of its interaction with the femur. For example, this can give an indication of the state of the ligaments of the knee joint or other anatomical features that affect the kinematic behaviour of the patella. The trajectory of the patella relative to the femur can be displayed together with the original trajectory 'natural' trajectory of the patella to see how they compare. This can be done by displaying a graphical representation of the free running trajectory together with a graphical representation of the original natural trajectory overlaid on each other and/or over a graphical representation of the knee joint and/or at least the femoral trial implant.

Also, the displacement of the second component relative to the first component as a function of the extension/flexion of the knee joint can be displayed. By tracking the trajectories of first and second components, and determining their separations the medial-lateral displacement of the second component relative to the first can be determined. For example, it may be found that the medial-lateral displacement of the first and second components may be +2 mm at a first position and +4 mm at a second position. Hence, it can be determined that a good compromise position for the actual patella implant would be +3 mm from the current position of the first component.

In an embodiment in which the moveable second component includes a trackable marker but the first component does not, then it is possible to determine the medial-lateral displacement by registering or capturing the initial position of the moveable second component, when centred on the first component, prior to tracking its trajectory. The initially registered central position corresponds to the 'zero displacement' position and then the displacement of the moveable component can be determined relative to that zero position.

At step 224, the second component can be off set by the amount determined for the free running flexion/extension cycle, e.g. +3 mm as in the example above, and then the second component locked so that it cannot slide relative to the first component. Then at step 226, the patella and components of the patella trial are again tracked as the knee is articulated through a flexion-extension cycle. Again a graphical representation of the trajectory of the patella relative to the femoral component can be displayed to the user, together with an indication of the displacement of the current trajectory from the original 'natural' trajectory.

At step 228 it is determined whether the trajectory of the patella with the trial at its current off set position is acceptable or not. If it is determined that some adjustment to the patella medial-lateral position may be helpful, then the method proceeds to step 230, at which the medial-lateral position of the trial may be adjusted by unlocking, adjusting and then re-locking the trial, or moving the first component of the trial on the patella, or adjusting the position of the femoral component, or any combination thereof. After any adjustment, if required. Then at step 220 either a further free running trajectory can be captured or alternatively, the patella trial implant can be locked to prevent the second component from translating in the medial-lateral direction. Then the position of the patella is again tracked as the knee is articulated between flexion and extension to determine the trajectory of the patella relative to the femoral component. Again, the trajectory and medial-lateral displacement is assessed at step 228 to determine whether the trajectory of the patella for the patella trial at the current medial-lateral position is acceptable or not.

For example, the captured trajectory may show that the patella is displaced too far in the medial or lateral directions or is making unwanted contacted with a part of the femoral component or is straining a ligament or other soft tissue or may otherwise be harmful to the joint if the current patella trial implant position were used for the actual patella implant.

In general, comparing the trajectory for the locked trial implant with the trajectory of the original 'natural' implant can help in seeing what patella trajectory the planned implant positions would achieve relative to what patella trajectory the patella originally had.

If the trajectory is not acceptable, for whatever reason, then at step 230, the medial-lateral position of the trial can be altered and re-locked and/or the position of the femoral trial component can be adjusted so as to try and improve the kinematic performance of the knee joint. The method then returns and further iterations of steps 220, 222, 224, 226, 228 and 230 can be carried out as required until the surgeon has settled on a medial-lateral position for the patella implant that results in an acceptable patella trajectory.

Then at step 232, holes are drilled in the patella to accept fastening posts for the actual patella implant at the determined medial-lateral off set position. Patella implants are generally known in the art and are generally similar to the patella trial described herein, except they do not allow for relative translation of two components and have pegs extending from a rear surface for securing the implant to the posterior face of the patella. The shape of the femur contacting part should be generally the same shape as the corresponding part of the trial. The positions of the holes in the patella for the pegs can be determined in a number of ways. For example, holes having the same spacing as the pegs can be provided in the second component, with corresponding slots in the first component so that a guide wire or other marker can be used to mark the positions on the resected surface of the patella at which the holes should be drilled. Alternatively, the offset of the second component relative to the first component can be used to determine the correct position for the actual patella implant, if the spacing of the pins on the back of the trial corresponds to the spacing of the pegs on the back of the actual implant.

Then at step 234, the actual tibial, femoral and patella implant components are implanted in the patient and cemented in place. If the position of the patella implant does not correspond to the position of the patella trial implant then the patella implant is registered at step 236 with the CAS system prior to the final tracking step 238. A number of methods can be used to register the patella implant. For example, the positions of three dimples on the patella implant having a known geometry and a known positional relationship relative to the patella implant can be identified using a trackable pointer. Then, at step 238 the trajectory of the patella relative to the femoral component is verified by again tracking the patella as the knee is articulated to determine what the actual trajectory of the patella is for the prosthetic knee joint. The trajectory can be verified by being compared with any of the trajectories captured previously, and in particular with the original 'natural' trajectory. The comparison can be visual or numerical, e.g. by calculating a measure of the difference between the final trajectory and a previous trajectory.

Hence, using the trial patella implant device of the present invention, the positioning of the patella implant and/or of the femoral component can be optimised to provide a desired kinematic performance of the knee joint.

The invention claimed is:

1. A method for assessing the positioning of a patella implant for a knee joint of a patient during a navigated knee surgical procedure, the knee joint having a femoral part, a tibial part and a patella, the method comprising:

attaching a first component of a trial patella implant to the posterior of the patella, the trial patella implant having a second component that translates relative to the first component in the medial-lateral direction when the first component is attached to the patella, wherein at least one of the first component and the second component comprises a marker;

tracking the location of the trial implant patella as the knee joint is articulated while the second component is free to translate relative to the first component by communicating tracking data transmitted by the marker during the articulation of the knee joint to a computer;

tracking the location of the trial implant patella as the knee joint is articulated while the second component is fixed in the medial-lateral direction relative to the first component by communicating tracking data transmitted by the marker during the articulation of the knee joint to a computer; and determining (i) a first trajectory of the trial implant patella based on the tracking data communicated to the computer while the second component is free to translate relative to the first component using the computer and (ii) a second trajectory of the trial implant patella based on the tracking data communicated to the computer while the second component is fixed in the medial-lateral direction relative to the first component using the computer; and determining the medial-lateral displacement of the second component relative to the patella over at least a part of the first trajectory or the second trajectory using the computer.

2. The method of claim 1, further comprising the step of using the computer to compare the first trajectory to the second trajectory.

3. The method of claim 1, wherein the trajectory is determined relative to a femoral part or tibial part of the knee joint.

\* \* \* \* \*